(12) United States Patent
Cho et al.

(10) Patent No.: US 8,431,656 B2
(45) Date of Patent: Apr. 30, 2013

(54) CURABLE CYCLIC PHOSPHAZENE COMPOUND AND METHOD OF PREPARING THE SAME

(75) Inventors: Jae Choon Cho, Gyunggi-do (KR); Do Yeung Yoon, Seoul (KR); Ji Young Chang, Seoul (KR); Ho Lim, Gyunggi-do (KR); Hwa Young Lee, Gyunggi-do (KR)

(73) Assignees: Samsung Electro-Mechanics Co. Ltd., Suwon, Gyunggi-Do (KR); SNU R&DB Foundation, Seoul (KR)

( * ) Notice: Subject to any disclaimer, the term of this patent is extended or adjusted under 35 U.S.C. 154(b) by 541 days.

(21) Appl. No.: 12/511,818

(22) Filed: Jul. 29, 2009

(65) Prior Publication Data
US 2011/0028584 A1    Feb. 3, 2011

(51) Int. Cl.
*C08L 85/02* (2006.01)
*C08G 79/02* (2006.01)
*C08F 283/00* (2006.01)

(52) U.S. Cl.
USPC ........... 525/538; 528/398; 528/399; 528/400; 524/97; 524/95; 524/96; 522/167; 522/168; 522/171

(58) Field of Classification Search .................. 522/171, 522/167, 168; 528/398, 399, 400; 526/528; 524/97, 95, 96
See application file for complete search history.

(56) References Cited

U.S. PATENT DOCUMENTS

| 5,115,082 | A | 5/1992 | Mercer et al. |
| 5,405,677 | A | 4/1995 | Griffith et al. |

FOREIGN PATENT DOCUMENTS

| JP | 3-282874 | 12/1991 |
| JP | 60-104129 | 6/1995 |
| JP | 10-053596 | 2/1998 |
| JP | 2001-64292 | 3/2001 |
| KR | 10-2005-0042810 | 5/2005 |

OTHER PUBLICATIONS

Allcock et al. New Polyphosphazenes with Unsaturated Side Groups: Use as Reaction Intermediates, Cross-Linkable Polymers, and Components of Interpenetrating Polymer Networks. Macromolecules, 1996, 29 (8), 2721-2728.*
Allcock et al. Crosslinking reactions for Conversion of Polyphosphazenes into Useful Materials. Chemistry of Materials. 1994, 6 (9), 1476-1491.*
Inoue et al. High-Conductivity Electrolytes Composed of Polystryene Carrying Pendant Oligo(oxyethylene)cyclotriphsophazenes and LiCO4. Journal of the American Chemical Society. 1991, 113, 7609-7613.*
Inoue et al. Preparation and polymerization of 2-(p-methacryloyloxy-methylphenoxy)-2,4,4,6,6-pentakis(2,2,2-trifluoroethoxy)-cyclotriphosphazene. Makromolecular Rapid Communications. 11, 467-470 (1990).*
Inoue et al. Synthesis and Functionality of Cyclophophazene-based Polymers. Bulletine of the Chemical Society of Japan. 74, No. 8 (2001) pp. 1381-1395.*
Office Action from counterpart Japanese Patent Application No. 2009-175623, mailed Jan. 31, 2012, 4 pages.

* cited by examiner

*Primary Examiner* — Sanza McClendon
(74) *Attorney, Agent, or Firm* — Blakely Sokoloff Taylor & Zafman LLP (57) ABSTRACT

Disclosed herein is a curable cyclic phosphazene compound having a low dielectric constant, a low dielectric loss index and high thermal stability, and a method of preparing the same. The curable cyclic phosphozene polymer prepared using the compound has a low dielectric constant and excellent thermal properties, compared to conventional phosphozene polymers.

3 Claims, 7 Drawing Sheets

CURABLE CYCLIC PHOSPHAZENE COMPOUND AND METHOD OF PREPARING THE SAME

BACKGROUND OF THE INVENTION

1. Technical Field

The present invention relates to a curable cyclic phosphazene compound and a method of preparing the same, and, more particularly, to a curable cyclic phosphazene compound having a low dielectric constant, a low dielectric loss index and high thermal stability, and a method of preparing the same.

2. Description of the Related Art

Recently, printed circuit boards (PCBs) and semiconductor devices have been problematic in that signal loss and signal delay phenomena are caused by the miniaturization and high-integration of devices and the increase in frequency of used signals. In order to solve this problem, conventionally, electric resistance has been decreased by changing a wiring material from an aluminum conductor to a copper conductor, and it has been required to develop low dielectric materials.

In particular, a phenol resin, an epoxy resin and the like have been used to make a conventional insulator, but they cannot be used for PCBs and the like because of the above-mentioned problem. Therefore, it is predicted that a material having a low dielectric constant and a low dielectric loss, which is developed in the present invention, be used as an insulator.

With the miniaturization, high-integration and high-densification of semiconductor devices and printed circuit boards (PCBs), insulating materials having a low dielectric constant of 3.0 or less are increasingly required because they can reduce signal delay time.

Fluorine resins have been actively developed because they have excellent resistance to heat and chemicals as well as a low dielectric constant.

For example, Japanese Unexamined Patent Application Publication Nos. 1985-104129 and 1991-282874 disclose a fluorine-containing polyimide resin (dielectric constant: 2.2~2.8), U.S. Pat. No. 5,115,082 discloses a fluorine-containing poly(arylene ether) resin (dielectric constant: 2.4~2.6), and U.S. Pat. No. 5,405,677 discloses a fluorine-containing aromatic resin (dielectric constant: 2.1~2.5).

However, since a process of producing a printed circuit board is performed at a high temperature of 200~450, a fluorine resin having a low glass transition temperature and having a low elastic modulus and a high linear expansion coefficient at high temperature has serious problems related to the insurance of the reliability of a printed circuit board.

Hence, attempts to develop materials having a low dielectric constant and a low dielectric loss index have been made. Typical examples of the materials include BCB (benzocyclobutene), SiLK (trade name of Dow Chemical Company) and the like.

However, these materials are also problematic in that they cannot be easily prepared, and in that they have low interface adhesion, thus deteriorating the mechanical properties of devices.

In particular, when SiLK, which is an organic material having a low dielectric constant, is used, a new process of accurately controlling the width and depth of trenches or via-holes is additionally required.

SUMMARY OF THE INVENTION

Therefore, present inventors have made efforts to develop a material having a low dielectric constant, a low dielectric loss index and high thermal stability using a phosphazene compound which is well-known as a nonflammable material. Further, they have introduced heat-curable reaction groups into a phosphazene compound in order to impart curability to the phosphazene compound, thereby completing the present invention.

Accordingly, the present invention provides a curable cyclic phosphazene compound having a low dielectric constant, a low dielectric loss index and high thermal stability, and a method of preparing the same.

Further, the present invention provides a phosphazene polymer prepared using the curable cyclic phosphazene compound.

In order to accomplish the above objects, it was found that cyclic phosphazene having 6 substitution sites is substituted with 2~6 heat-curable reaction groups and other various substituents, so that the degree of cure, molecular polarization and free volume of the cyclic phosphazene can be adjusted, thereby preparing a material having a low dielectric constant, a low dielectric loss index, high thermal stability and high interface adhesion.

That is, the present invention provides a curable cyclic phosphazene material substituted with only aromatic compounds, a curable cyclic phosphazene material substituted with aliphatic compounds and aromatic compounds in a predetermined ratio, and synthesis methods thereof. Hereinafter, the present invention will be described in more detail as follows.

A curable cyclic phosphazene compound substituted with aliphatic and aromatic compounds according to the present invention has a structure represented by Formula (I) below:

(I)

wherein n is 3, $R^1$ and $R^2$ are identical to or different from each other, and the sum of the numbers of $R^1$ and $R^2$ is 6;

$R^1$ is any one substituent selected from the group (I) consisting of methoxy, ethoxy, propyloxy, trifluoroethoxy, 1-adamantanemethoxy, 1-adamantaneethoxy, 2-norbornanemethoxy, phenoxy, 4-methylphenoxy, 4-phenylphenoxy, 1-adamantanoxy, norborneoxy, decahydronaphthalene-2-oxy and naphtalene-2-oxy, and the number of the selected $R^1$ is 0~4; and $R^2$ is any one curable substituent selected from the group (II) consisting of 4-vinylphenoxy, 4-ethynylphenoxy, 4'-vinyl-4-biphenyloxy, 4'-ethynyl-4-biphenyloxy and 4-(phenylethynyl)phenoxy), and the number of the selected $R^2$ is 2~6.

Preferably, the compound, represented by Formula (I) above, may be selected from the compounds consisting of:

(1) a compound which includes 2~6 4-vinylphenoxy groups and 0~4 substituents selected from the group (I);

(2) a compound which includes 2~6 4-ethynylphenoxy groups and 0~4 substituents selected from the group (I);

(3) a compound which includes 2~6 4'-vinyl-4-biphenyloxy groups and 0~4 substituents selected from the group (I);

(4) a compound which includes 2~6 4'-ethynyl-4-biphenyloxy groups and 0~4 substituents selected from the group (I);

(5) a compound which includes 2~6 4-(phenylethynyl) phenoxy groups and 0~4 substituents selected from the group (I).

The curable cyclic phosphazene compound, represented by Formula (I), can be prepared using any one of the following two methods.

A first method of preparing the curable cyclic phosphazene compound includes:

1) converting a small amount of a compound represented by Formula II below, the amount being less than its equivalent, into sodium oxide using a base and then reacting the sodium oxide with hexachlorocyclotriphosphazene in an organic solvent to obtain a phosphazene-containing organic solution;

2) adding sodium alkoxide prepared by treating a compound represented by Formula III below with NaH or Na to the obtained phosphazene-containing organic solution and then reacting the sodium alkoxide with phosphazene to obtain a phosphazene compound; and 3) separating the obtained curable phosphazene.

$R^1$—H (II)

$R^3$—H (III)

wherein $R^1$ is defined as above, and $R^3$ is selected from the group consisting of 4-vinylphenoxy, 4'-vinyl-4-biphenyloxy and 4-(phenylethynyl)phenoxy.

A second method of preparing the curable cyclic phosphazene compound includes:

1) converting a small amount of a compound represented by Formula II below, the amount being less than its equivalent, into sodium oxide using a base and then reacting the sodium oxide with hexachlorocyclotriphosphazene in an organic solvent to obtain a phosphazene-containing organic solution;

2) adding sodium alkoxide prepared by treating a compound represented by Formula IV below with NaH or Na to the obtained phosphazene-containing organic solution and then reacting the sodium alkoxide with phosphazene to obtain a phosphazene compound;

3) dissolving the obtained phosphazene compound in a methanol solution and then treating the phosphazene compound with KOH and thus removing a trimethylsilyl group to obtain curable phosphazene; and 4) separating the obtained curable phosphazene.

$R^1$—H (II)

$R^4$—H (IV)

wherein $R^1$ is defined as above, and $R^4$ is selected from the group consisting of 4-trimethylsilylethynylphenoxy and 4'-trimethylsilylethynyl-4-biphenyloxy.

In this method, in the step 1), the number of the substituents may be adjusted by controlling reaction conditions.

Preferably, the number of the substituents may be adjusted by controlling a reflux period in consideration of the reactivity of substituents.

Generally, the reflux period is 12 hours~3 days, and can be controlled depending on the kinds of substituents and reaction conditions.

Further, 1,4-dioxane is used as the organic solvent.

Further, the polymerization reaction of cross-linking the curable phosphazene compounds may be performed by heating and then curing the curable phosphazene compounds or by using cupric acetate (Cu(II)-acetate) as a catalyst.

The heat-curable reaction group includes an acetylene group and a vinyl group.

The heat-curable reaction group included in the phosphazene compound is thermally cured at 150~200° C. In particular, the acetylene group can be thermally cured in solid phase as well as in liquid phase. Further, the reaction product is very thermally stable.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, the present invention will be described in detail with reference to the following Examples. However, the scope of the present invention is not limited thereto.

The $^1$H and $^{13}$C NMR spectrum analysis of the compound of the present invention was performed using a BRUKER Avance DPX-300 and Avance 500 spectrometer, the thermogravimetric analysis thereof was performed using a Q50 thermogravimetric analyzer (TGA) manufactured by TA Corp., and the differential scanning calorimetry measurement thereof was performed using a modulated Q10 differential scanning calorimeter manufactured by TA Corp.

EXAMPLE 1

A compound represented by Formula (I) in which $R^1$ and $R^2$ include a 1-adamantanemethoxy group and a 4'-ethynyl-4-biphenyloxy group.

0.26 g of NaH was mixed with a solution in which 1.70 g of 1-adamantanemethanol was dissolved in 1,4-dioxane (50 mL), and was then stirred at room temperature for 2 hours, and then a solution in which 1.00 g of hexachlorocyclotriphosphazene was dissolved in 1,4-dioxane (50 mL) was added thereto and then refluxed for 3 days to prepare a reaction solution. Subsequently, 0.26 g of NaH was mixed with a solution in which 2.90 g of 4'-trimethylsilylethynyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at 30° C. for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.92-7.38 (overlap, C$_6$H$_4$, 24H), 3.48 (s, ≡CH, 3H), 3.15 (d, —OCH$_2$—, 6H), 1.24-2.17 (m, admantyl, 45H)

$^{31}$P NMR(CDCl$_3$):δ=16.80-17.63, 13.6-14.2, 10.90-10.82

EXAMPLE 2

A compound represented by Formula (I) in which $R^1$ and $R^2$ include a 1-adamantanemethoxy group and a 4-ethynylphenoxy group.

0.26 g of NaH was mixed with a solution in which 1.70 g of 1-adamantanemethanol was dissolved in 1,4-dioxane (50 mL), and was then stirred at room temperature for 2 hours, and then a solution in which 1.00 g of hexachlorocyclotriphosphazene was dissolved in 1,4-dioxane (50 mL) was added thereto and then refluxed for 3 days to prepare a reaction solution. Subsequently, 0.26 g of NaH was mixed with a solution in which 1.50 g of 4-trimethylsilylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at 30° C. for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.92-7.38 (overlap, C$_6$H$_4$, 24H), 3.48 (s, ≡CH, 3H), 3.15 (d, —OCH$_2$—, 6H), 1.24-2.17 (m, admantyl, 45H)

$^{31}$P NMR(CDCl$_3$):δ=16.80-17.63, 13.6-14.2, 10.90-10.82

EXAMPLE 3

A compound represented by Formula (I) in which $R^1$ and $R^2$ include a 1-adamantanemethoxy group and a 4-(phenylethynyl)phenoxy group.

0.26 g of NaH was mixed with a solution in which 1.70 g of 1-adamantanemethanol was dissolved in 1,4-dioxane (50 mL), and was then stirred at room temperature for 2 hours, and then a solution in which 1.00 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 2.80 g of 4-phenylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.59 (overlap, C$_6$H$_4$, 30H), 3.15 (d, —OCH$_2$—, 6H), 1.24-2.17 (m, admantyl, 45H)

$^{31}$P NMR(CDCl$_3$):δ=16.80-17.63, 13.6-14.2 (overlap, —CH$_2$O—P—OAr, 1P), 10.90-10.82

EXAMPLE 4

A compound represented by Formula (I) in which $R^1$ and $R^2$ include a 1-adamantanemethoxy group and a 4'-vinyl-4-biphenyloxy group.

0.26 g of NaH was mixed with a solution in which 1.70 g of 1-adamantanemethanol was dissolved in 1,4-dioxane (50 mL), and was then stirred at room temperature for 2 hours, and then a solution in which 1.00 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 2.84 g of 4'-vinyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.59 (overlap, C$_6$H$_4$, 30H), 6.63 (m, Ar—CH=, 3H), 5.61(d, =CH$_2$, 3H), 5.18(m, =CH$_2$, 3H), 3.15 (d, —OCH$_2$—, 6H), 1.24-2.17 (m, admantyl, 45H)

$^{31}$P NMR(CDCl$_3$):δ=16.80-17.63, 13.6-14.2, 10.90-10.82

EXAMPLE 5

A compound represented by Formula (I) in which $R^1$ and $R^2$ include a 1-adamantanemethoxy group and a 4-vinylphenoxy group.

0.26 g of NaH was mixed with a solution in which 1.70 g of 1-adamantanemethanol was dissolved in 1,4-dioxane (50 mL), and was then stirred at room temperature for 2 hours, and then a solution in which 1.00 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 1.25 g of 4-vinylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.59 (overlap, C$_6$H$_4$, 12H), 6.63 (m, Ar—CH=, 3H), 5.61(d, =CH$_2$, 3H), 5.18(m, =CH$_2$, 3H), 3.15 (d, —OCH$_2$—, 6H), 1.24-2.17 (m, admantyl, 45H)

$^{31}$P NMR(CDCl$_3$):δ=16.80-17.63, 13.6-14.2, 10.90-10.82

EXAMPLE 6

A compound represented by Formula (I) in which $R^1$ and $R^2$ include a 2-nornornanemethoxy group and a 4'-ethynyl-4-biphenyloxy group.

0.45 g of NaH was mixed with a solution in which 2.36 g of 2-norbornanemethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 5.00 g of 4'-trimethylsilylethynyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.92-7.38 (overlap, C$_6$H$_4$, 24H), 3.48 (s, ≡CH, 3H), 3.62 (d, —OCH$_2$—, 6H), 1.43-2.13(overlap, norbornyl, 32H)

$^{31}$P NMR(CDCl$_3$):δ=16.80-17.63, 13.6-14.2, 10.90-10.82

EXAMPLE 7

A compound represented by Formula (I) in which $R^1$ and $R^2$ include a 2-nornornanemethoxy group and a 4-ethynylphenoxy group.

0.45 g of NaH was mixed with a solution in which 2.36 g of 2-norbornanemethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 3.14 g of 4-trimethylsilylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.92-7.35 (overlap, C$_6$H$_4$, 12H), 3.48 (s, ≡CH, 3H), 3.62 (d, —OCH$_2$—, 6H), 1.43-2.13(overlap, norbornyl, 32H)

$^{31}$P NMR(CDCl$_3$):δ=16.80-17.63, 13.6-14.2, 10.90-10.82

EXAMPLE 8

A compound represented by Formula (I) in which $R^1$ and $R^2$ include a 2-nornornanemethoxy group and a 4-(phenylethynyl)phenoxy group.

0.45 g of NaH was mixed with a solution in which 2.36 g of 2-norbornanemethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 5.20 g of 4-phenylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=7.59 (overlap, C$_6$H$_4$, 6H), 7.41(overlap, C$_6$H$_4$, 12H), 6.91(overlap, C$_6$H$_4$, 6H), 3.48 (s, ≡CH, 3H), 3.62 (d, —OCH$_2$—, 6H), 1.43-2.13(overlap, norbornyl, 32H)

$^{31}$P NMR(CDCl$_3$):δ=16.80-17.63, 13.6-14.2, 10.90-10.82

EXAMPLE 9

A compound represented by Formula (I) in which $R^1$ and $R^2$ include a 2-nornornanemethoxy group and a 4'-vinyl-4-biphenyloxy group.

0.45 g of NaH was mixed with a solution in which 2.36 g of 2-norbornanemethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 5.23 g of 4'-vinyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.59 (overlap, C$_6$H$_4$, 24H), 6.63 (m, Ar—CH=, 3H), 5.61(d, =CH$_2$, 3H), 5.18(m, =CH$_2$, 3H), 3.62 (d, —OCH$_2$—, 6H), 1.43-2.13(overlap, norbornyl, 32H)

$^{31}$P NMR(CDCl$_3$):δ=16.80-17.63, 13.6-14.2, 10.90-10.82

EXAMPLE 10

A compound represented by Formula (I) in which R$^1$ and R$^2$ include a 2-nornornanemethoxy group and a 4-vinylphenoxy group.

0.45 g of NaH was mixed with a solution in which 2.36 g of 2-norbornanemethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 3 days to prepare a reaction solution. Subsequently, 0.45 g of NaH was mixed with a solution in which 5.23 g of 4-vinylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.59 (overlap, C$_6$H$_4$, 24H), 6.63 (m, Ar—CH=, 3H), 5.61(d, =CH$_2$, 3H), 5.18(m, =CH$_2$, 3H), 3.62 (d, —OCH$_2$—, 6H), 1.43-2.13(overlap, norbornyl, 32H)

$^{31}$P NMR(CDCl$_3$):δ=16.80-17.63, 13.6-14.2, 10.90-10.82

EXAMPLE 11

A compound represented by Formula (I) in which R$^1$ and R$^2$ include a trifluoroethoxy group and a 4'-ethynyl-4-biphenyloxy group.

0.39 g of NaH was mixed with a solution in which 1.62 g of trifluoroethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 2 days to prepare a reaction solution. Subsequently, 0.45 g of NaH was mixed with a solution in which 7.18 g of 4'-trimethylsilylethynyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.91-7.59 (overlap, C$_6$H$_4$, 24H), 4.05 (m, —OCH$_2$—, 6H), 3.48 (s, ≡CH, 3H )

$^{31}$P NMR(CDCl$_3$):δ=16.80-17.63, 13.6-14.2, 10.90-10.82

EXAMPLE 12

A compound represented by Formula (I) in which R$^1$ and R$^2$ include a trifluoroethoxy group and a 4-ethynylphenoxy group.

0.39 g of NaH was mixed with a solution in which 1.62 g of trifluoroethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 2 days to prepare a reaction solution. Subsequently, 0.65 g of NaH was mixed with a solution in which 5.13 g of 4-trimethylsilylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.92-7.38 (overlap, C$_6$H$_4$, 12H), 4.05 (m, —OCH$_2$—, 6H), 3.48 (s, ≡CH, 3H)

$^{31}$P NMR(CDCl$_3$):δ=16.80-17.63, 13.6-14.2, 10.90-10.82

EXAMPLE 13

A compound represented by Formula (I) in which R$^1$ and R$^2$ include a trifluoroethoxy group and a 4-(phenylethynyl) phenoxy group.

0.39 g of NaH was mixed with a solution in which 1.62 g of trifluoroethanol was dissolved in 1,4-dioxane (50 mL), and was then stirred at room temperature for 3 hours, and then a solution in which 1.84 g of hexachlorocyclotriphosphazene was dissolved in 1,4-dioxane (50 mL) was added thereto and then refluxed for 2 days to prepare a reaction solution. Subsequently, 0.68 g of NaH was mixed with a solution in which 5.23 g of 4-phenylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.92-7.38 (overlap, C$_6$H$_4$, 27H), 4.05 (m, —OCH$_2$—, 6H)

$^{31}$P NMR(CDCl$_3$):δ=16.80-17.63, 13.6-14.2, 10.90-10.82

EXAMPLE 14

A compound represented by Formula (I) in which R$^1$ and R$^2$ include a trifluoroethoxy group and a 4'-vinyl-4-biphenyloxy group.

0.42 g of NaH was mixed with a solution in which 1.74 g of trifluoroethanol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 5.68 g of 4'-vinyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.59 (overlap, C$_6$H$_4$, 24H), 6.63 (m, Ar—CH=, 3H), 5.61(d, =CH$_2$, 3H), 5.18(m, =CH$_2$, 3H), 4.05 (d, —OCH$_2$—, 6H)
$^{31}$P NMR(CDCl$_3$):δ=16.80-17.63, 13.6-14.2, 10.90-10.82

EXAMPLE 15

A compound represented by Formula (I) in which R$^1$ and R$^2$ include a trifluoroethoxy group and a 4-vinylphenoxy group.

0.42 g of NaH was mixed with a solution in which 1.74 g of trifluoroethanol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 3.48 g of 4-vinylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.90-7.56 (overlap, C$_6$H$_4$, 12H), 6.63 (m, Ar—CH=, 3H), 5.61(d, =CH$_2$, 3H), 5.18(m, =CH$_2$, 3H), 4.05 (d, —OCH$_2$—, 6H)
$^{31}$P NMR(CDCl$_3$):δ=16.80-17.63, 13.6-14.2, 10.90-10.82

EXAMPLE 16

A compound represented by Formula (I) in which R$^1$ and R$^2$ include a 4-phenylphenoxy group and a 4'-ethynyl-4-biphenyloxy group.

0.42 g of NaH was mixed with a solution in which 2.95 g of 4-phenylphenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 7.70 g of 4'-trimethylsilylethynyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.90-7.56 (overlap, C$_6$H$_4$, 51H), 5.61 (d, =CH$_2$, 3H), 5.18(m, =CH$_2$, 3H), 4.05 (d, —OCH$_2$—, 6H)
$^{31}$P NMR(CDCl$_3$):δ=10

EXAMPLE 17

A compound represented by Formula (I) in which R$^1$ and R$^2$ include a 4-phenylphenoxy group and a 4-ethynylphenoxy group.

0.42 g of NaH was mixed with a solution in which 2.95 g of 4-phenylphenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 5.51 g of 4-trimethylsilylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=6.90-7.56 (overlap, C$_6$H$_4$, 39H), 3.48 (s, =CH, 3H)
$^{31}$P NMR(CDCl$_3$):δ=10

EXAMPLE 18

A compound represented by Formula (I) in which R$^1$ and R$^2$ include a 4-phenylphenoxy group and a 4-(phenylethynyl) phenoxy group.

0.42 g of NaH was mixed with a solution in which 2.95 g of 4-phenylphenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 5.62 g of 4-phenylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.01 (overlap, C$_6$H$_4$, 12H), 7.38-7.62 (overlap, C$_6$H$_4$, 42H) $^{31}$P NMR(CDCl$_3$):δ=10

EXAMPLE 19

A compound represented by Formula (I) in which R$^1$ and R$^2$ include a 4-phenylphenoxy group and a 4'-vinyl-4-biphenyloxy group.

0.42 g of NaH was mixed with a solution in which 2.95 g of 4-phenylphenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 5.62 g of 4'-vinyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.01 (overlap, C$_6$H$_4$, 12H), 7.38-7.62 (overlap, C$_6$H$_4$, 39H) 6.63(m, =CH$_2$, 3H), 5.61(d, =CH$_2$, 3H), 5.18(d, =CH$_2$, 3H)
$^{31}$P NMR(CDCl$_3$):δ=10

EXAMPLE 20

A compound represented by Formula (I) in which R$^1$ and R$^2$ include a 4-phenylphenoxy group and a 4-vinylphenoxy group.

0.42 g of NaH was mixed with a solution in which 2.95 g of 4-phenylphenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.66 g of NaH was mixed with a solution in which 3.40 g of 4-vinylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=6.91-7.01 (overlap, C$_6$H$_4$, 12H), 7.38-7.62 (overlap, C$_6$H$_4$, 27H) 6.63(m, =CH$_2$, 3H), 5.61(d, =CH$_2$, 3H), 5.18(d, =CH$_2$, 3H)
$^{31}$P NMR(CDCl$_3$):δ=10

EXAMPLE 21

A compound represented by Formula (I) in which R$^1$ and R$^2$ include a phenoxy group and a 4'-ethynyl-4-biphenyloxy group.

0.42 g of NaH was mixed with a solution in which 1.83 g of phenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 7.70 g of 4'-trimethylsilylethynyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ=7.61-7.63(overlap, C$_6$H$_4$, 18H), 7.18-7.28(overlap, C$_6$H$_4$, 15) 7.01(m, C$_6$H$_4$, 6), 3.48(s, ≡CH, 3H)
$^{31}$P NMR(CDCl$_3$):δ=10

EXAMPLE 22

A compound represented by Formula (I) in which R$^1$ and R$^2$ include a phenoxy group and a 4-ethynylphenoxy group.

0.42 g of NaH was mixed with a solution in which 1.83 g of phenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 5.50 g of 4-trimethylsilylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel. Subsequently, KOH was mixed with a solution in which the separated compound was dissolved in methanol (50 mL) and tetrahydrofuran (THF) (50 mL), and was then stirred at room temperature for 12 hours. Subsequently, solids were removed from the mixture through a filtering process, and then a solvent was removed therefrom under reduced pressure to concentrate the mixture. Then, a final product was separated from the concentrated mixture through column chromatography.

$^1$H NMR(CDCl$_3$):δ 7.21-7.38(overlap, C$_6$H$_4$, 21) 6.92(m, C$_6$H$_4$, 6), 3.48(s, ≡CH, 3H)

$^{31}$P NMR(CDCl$_3$):δ=10

EXAMPLE 23

A compound represented by Formula (I) in which R$^1$ and R$^2$ include a phenoxy group and a 4-(phenylethynyl)phenoxy group.

0.42 g of NaH was mixed with a solution in which 1.83 g of phenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 5.62 g of 4-phenylethynylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=7.59(m, C$_6$H$_4$, 6H), 7.38-7.42(overlap, C$_6$H$_4$, 15H), 7.18-7.28(overlap, C$_6$H$_4$, 15H), 6.91(m, C$_6$H$_4$, 6)
$^{31}$P NMR(CDCl$_3$):δ=10

EXAMPLE 24

A compound represented by Formula (I) in which R$^1$ and R$^2$ include a phenoxy group and a 4'-vinyl-4-biphenyloxy group.

0.42 g of NaH was mixed with a solution in which 1.83 g of phenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 5.62 g of 4'-vinyl-4-biphenylol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=7.59-7.62(overlap, C$_6$H$_4$, 12H), 7.44 (m, C$_6$H$_4$, 6H), 7.18-7.28(overlap, C$_6$H$_4$, 15H) 6.91-7.01 (overlap, C$_6$H$_4$, 6H) 6.63(m, =CH$_2$, 3H), 5.61(d, =CH$_2$, 3H), 5.18(d, =CH$_2$, 3H)
$^{31}$P NMR(CDCl$_3$):δ=10

EXAMPLE 25

A compound represented by Formula (I) in which R$^1$ and R$^2$ include a phenoxy group and a 4-vinylphenoxy group.

0.42 g of NaH was mixed with a solution in which 1.83 g of phenol was dissolved in 1,4-dioxane (50 mL), and was then stirred at room temperature for 3 hours, and then a solution in which 2.00 g of hexachlorocyclotriphosphazene was dissolved in 1,4-dioxane (50 mL) was added thereto and then refluxed for 2 days to prepare a reaction solution. Subsequently, 0.70 g of NaH was mixed with a solution in which 3.48 g of 4-vinylphenol was dissolved in 1,4-dioxane (50 mL), and was then stirred for 1 hour, and was then added to the prepared reaction solution, and was then refluxed for 3 days to obtain a reaction product. Subsequently, salts were removed from the reaction product through a filtering process, and then a solvent was removed therefrom under reduced pressure to concentrate the reaction product. Then, a target compound was separated from the concentrated reaction product through column chromatography using silica gel.

$^1$H NMR(CDCl$_3$):δ=7.56(m, C$_6$H$_4$, 6H), 7.18-7.28(overlap, C$_6$H$_4$, 15H) 6.91-7.01(overlap, C$_6$H$_4$, 6H) 6.63(m, =CH$_2$, 3H), 5.61(d, =CH$_2$, 3H), 5.18(d, =CH$_2$, 3H)
$^{31}$P NMR(CDCl$_3$):δ=10

EXAMPLE 26

A compound represented by Formula (I) in which R$^1$ and R$^2$ each include a 4'-vinyl-4-biphenyloxy group.

1.0 g of NaH was mixed with a solution in which 8.10 g of 4'-vinyl-4-biphenylol was dissolved in 1,4-dioxane (50 mL), and was then stirred at room temperature for 1 hour, and then a solution in which 2.00 g of hexachlorocyclotriphosphazene was dissolved in 1,4-dioxane (50 mL) was added thereto and then refluxed for 3 days to prepare a reaction solution. Subsequently, salts were removed from the reaction solution through a filtering process, and then a solvent was removed therefrom under reduced pressure to concentrate the reaction solution. Then, a target compound was separated from the concentrated reaction solution through column chromatography using silica gel.

$^1$H NMR(CDCl$_3$):δ=7.59-7.62(m, C$_6$H$_4$, 24H), 7.44(m, C$_6$H$_4$, 12H) 6.91-7.01(overlap, C$_6$H$_4$, 12H) 6.63(m, =CH$_2$, 6H), 5.61(d, =CH$_2$, 6H), 5.18(d, =CH$_2$, 6H)
$^{31}$P NMR(CDCl$_3$):δ=10

EXAMPLE 27

A compound represented by Formula (I) in which R$^1$ and R$^2$ each include a 4-vinylphenoxy group.

1.0 g of NaH was mixed with a solution in which 5.0 g of 4-vinylphenol was dissolved in 1,4-dioxane (50 mL), and was then stirred at room temperature for 1 hour, and then a solution in which 2.00 g of hexachlorocyclotriphosphazene was dissolved in 1,4-dioxane (50 mL) was added thereto and then refluxed for 3 days to prepare a reaction solution. Subsequently, salts were removed from the reaction solution through a filtering process, and then a solvent was removed therefrom under reduced pressure to concentrate the reaction solution. Then, a target compound was separated from the concentrated reaction solution through column chromatography using silica gel.

$^1$H NMR(CDCl$_3$):δ=7.56(m, C$_6$H$_4$, 12H), 6.90(m, C$_6$H$_4$, 12H) 6.63(m, =CH$_2$, 6H), 5.61(d, =CH$_2$, 6H), 5.18(d, =CH$_2$, 6H)
$^{31}$P NMR(CDCl$_3$):δ=10

The monomers obtained from Examples 1 to 27 shall be designated as "C-1 to C-27", respectively.

Preparation Example 1

Preparation of a Polymer of the Present Invention

For example, a polymer of C-1 is prepared using two methods. First, a C-1 compound is heat-treated at a temperature of 150~200° C. for 2 hours, thus obtaining a cross-linked polymer. Second, a C-1 compound and 1 equivalent of cupric acetate (Cu(II)acetate) are mixed with a solution of pyridine and methanol, and then stirred at 70° C. for 10 hours to obtain a cross-linked polymer.

Preparation Example 2

Preparation of a Polymer of the Present Invention

For example, a polymer of C-27 is prepared using three methods. First, a C-27 compound is heat-treated at a temperature of 150~200° C. for 2 hours, thus obtaining a cross-linked polymer. Second, a C-27 compound is mixed with 4 wt % of AIBN (Azobisisobutyronitrile) and then heat-treated at a temperature of about 100° C. for 2 hours, thus obtaining a cross-linked polymer. Third, a C-27 compound is mixed with 4 wt % of DMPA (2,2-dimethoxy-2-phenyl acetophenone) and then photopolymerized using a high-pressure mercury lamp, thus obtaining a cross-linked polymer.

Preparation Example 3

Preparation of a Polymer of the Present Invention

For example, a polymer of a mixture of C-27 and styrene is prepared using two methods. First, a C-27 compound is mixed with a styrene monomer at a molar ratio of 3~10 to form a first mixture, and then the first mixture is mixed with 4 wt % of AIBN (Azobisisobutyronitrile) to form a second mixture, and then the second mixture is heat-treated at a temperature of about 100° C. for 2 hours to obtain a cross-linked polymer. Second, the first mixture is mixed with 4 wt % of DMPA (2,2-dimethoxy-2-phenyl acetophenone) to form a second mixture, and then the second mixture is photopolymerized using a high-pressure mercury lamp to obtain a cross-linked polymer.

Test Example 1

Figure 1:
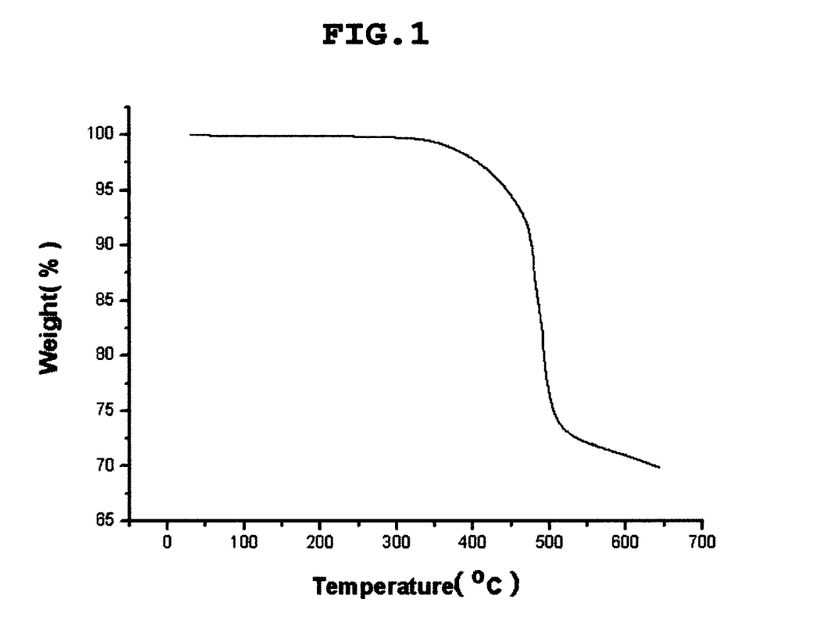
FIG. 1 is a graph showing the analysis results of a C-1 cross-linked body using a thermogravimetric analyzer (TGA) according to the present invention.
Figure 2:
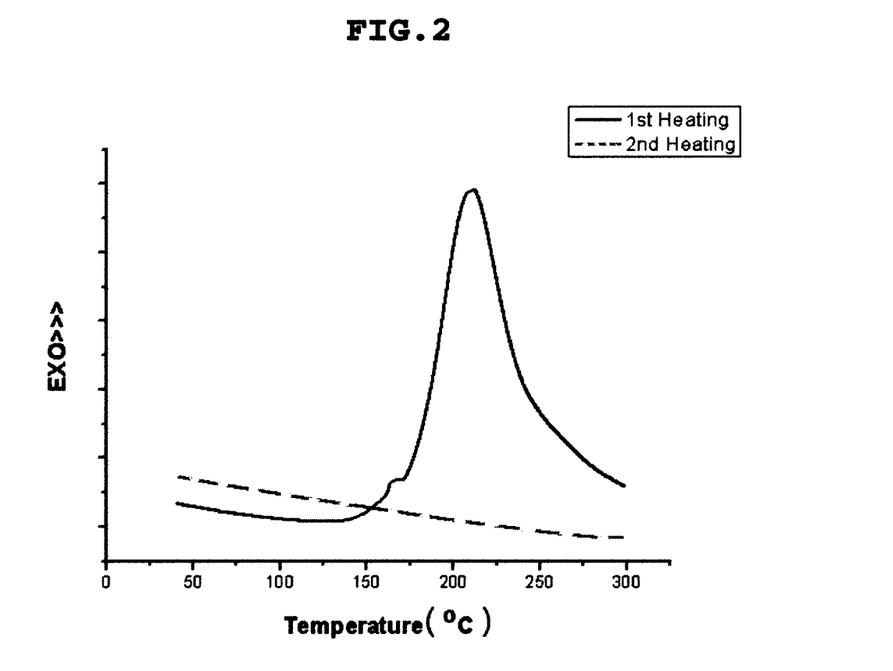
FIG. 2 is a graph showing the analysis results of a C-1 compound using a differential scanning calorimeter (DSC) according to the present invention.
Figure 3:
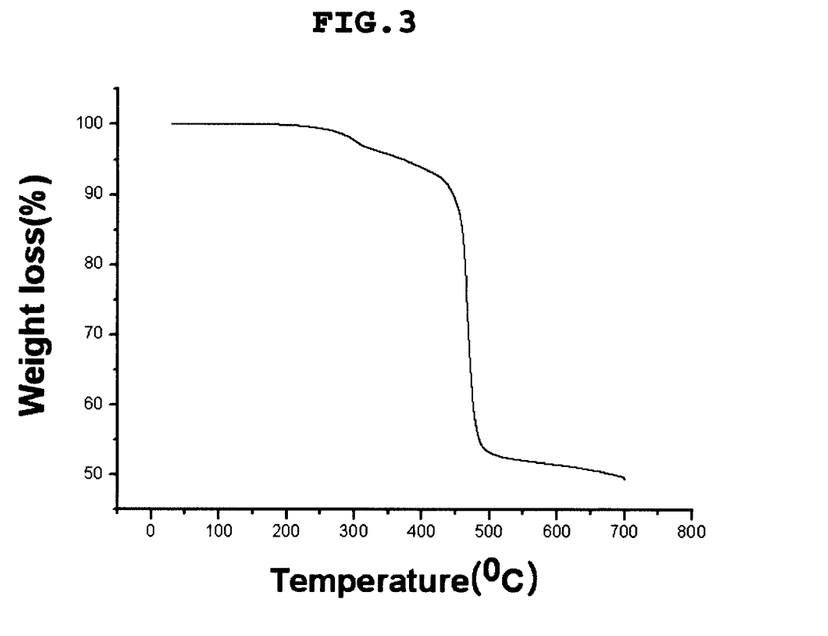
FIG. 3 is a graph showing the analysis results of a C-5 cross-linked body using a thermogravimetric analyzer (TGA) according to the present invention.
Figure 4:
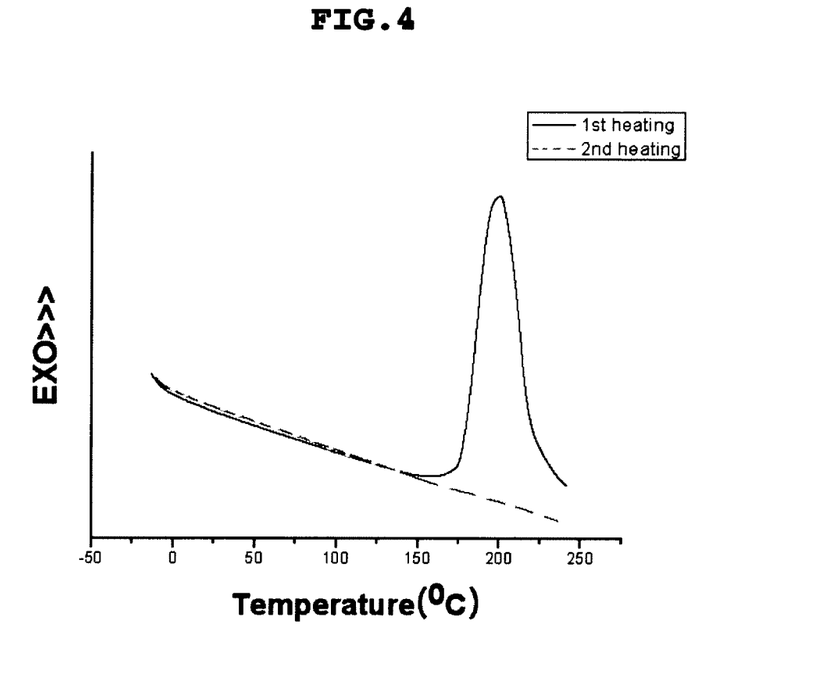
FIG. 4 is a graph showing the analysis results of a C-5 compound using a differential scanning calorimeter (DSC) according to the present invention.
Figure 5:
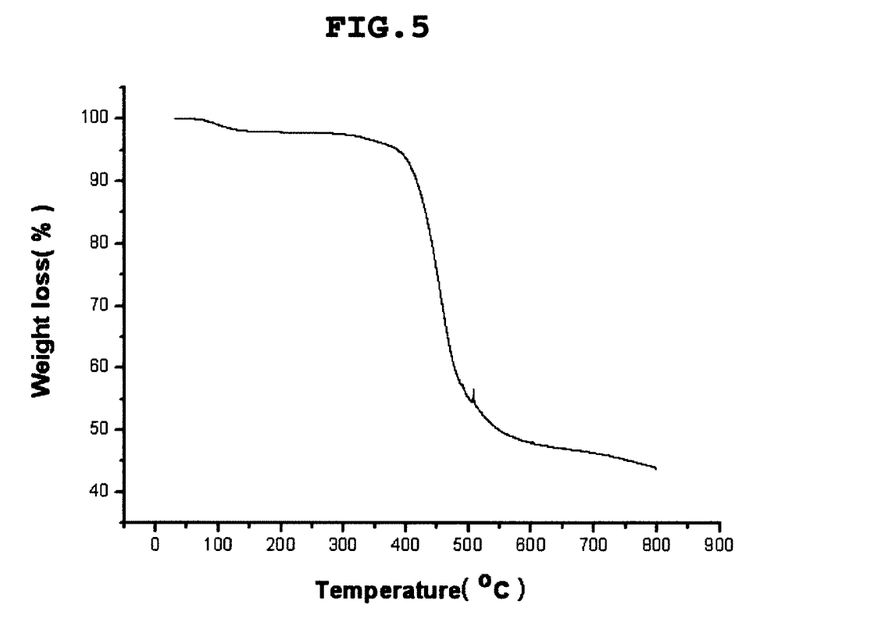
FIG. 5 is a graph showing the analysis results of a C-6 cross-linked body using a thermogravimetric analyzer (TGA) according to the present invention.
Figure 6:
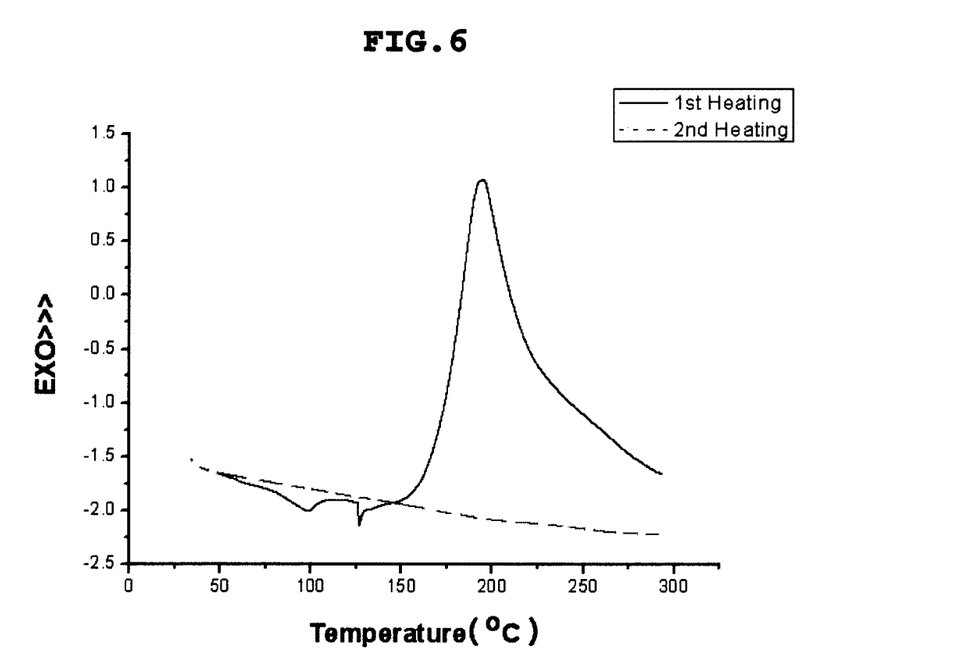
FIG. 6 is a graph showing the analysis results of a C-6 compound using a differential scanning calorimeter (DSC) according to the present invention.
Figure 7:
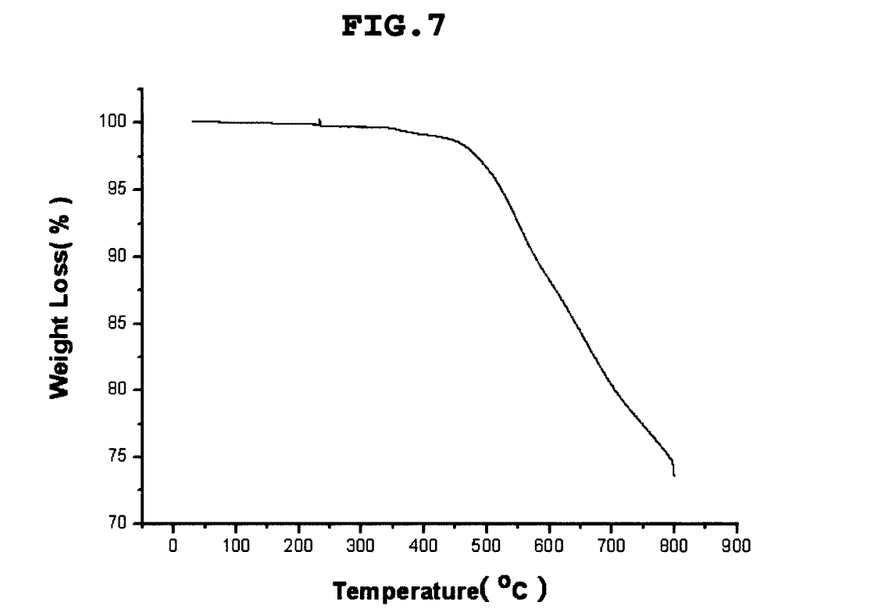
FIG. 7 is a graph showing the analysis results of a C-11 cross-linked body using a thermogravimetric analyzer (TGA) according to the present invention.
Figure 8:
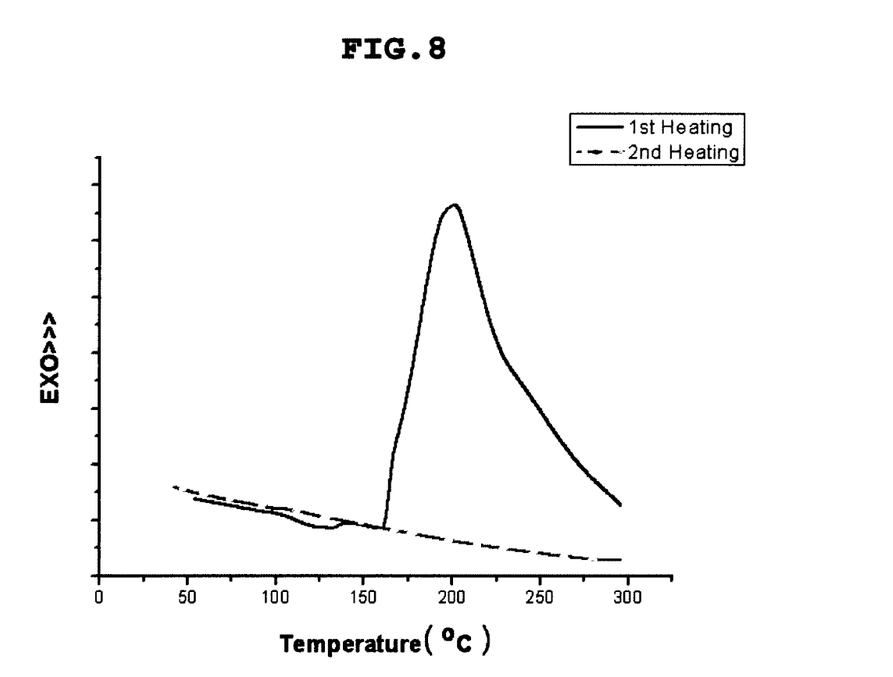
FIG. 8 is a graph showing the analysis results of a C-11 compound using a differential scanning calorimeter (DSC) according to the present invention.
Figure 9:
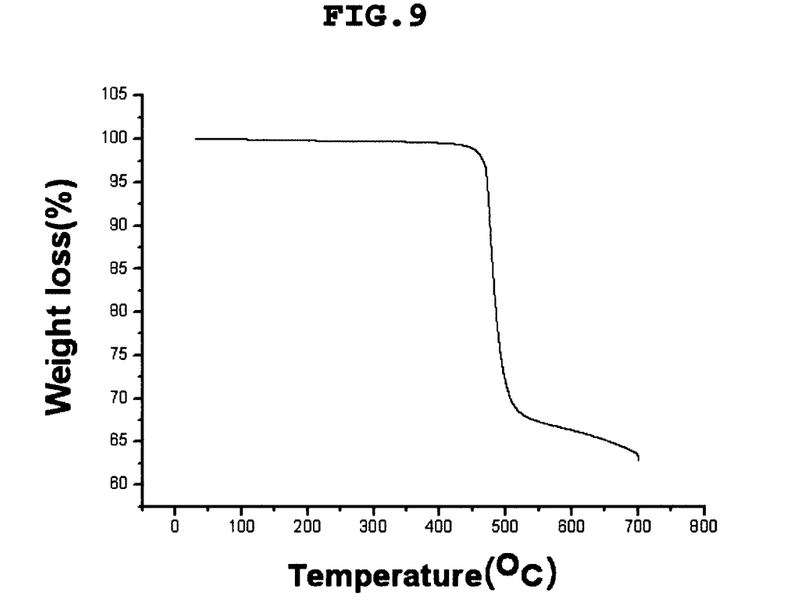
FIG. 9 is a graph showing the analysis results of a C-27 cross-linked body using a thermogravimetric analyzer (TGA) according to the present invention.
Figure 10:
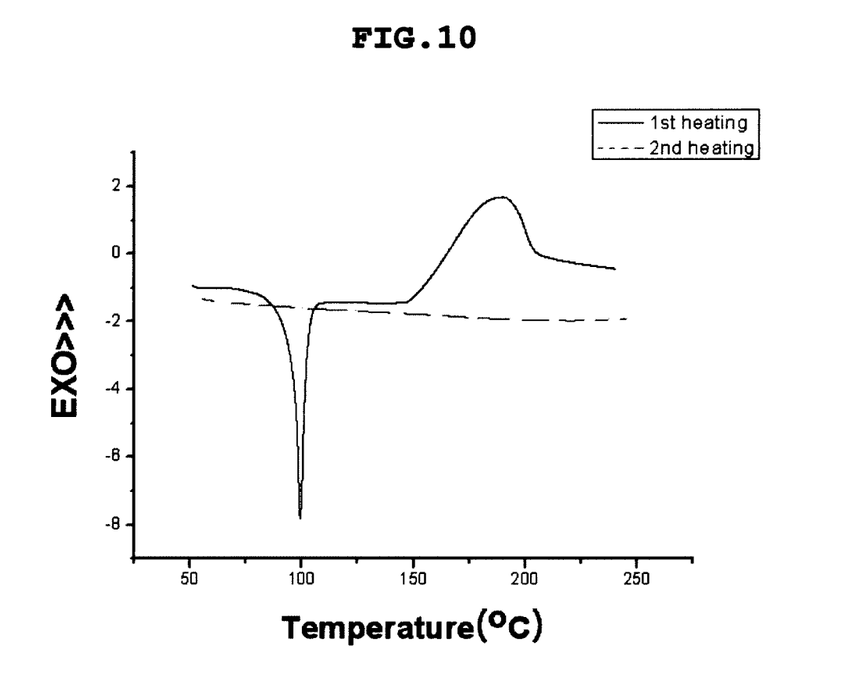
FIG. 10 is a graph showing the analysis results of a C-27 compound using a differential scanning calorimeter (DSC) according to the present invention.
Figure 11:
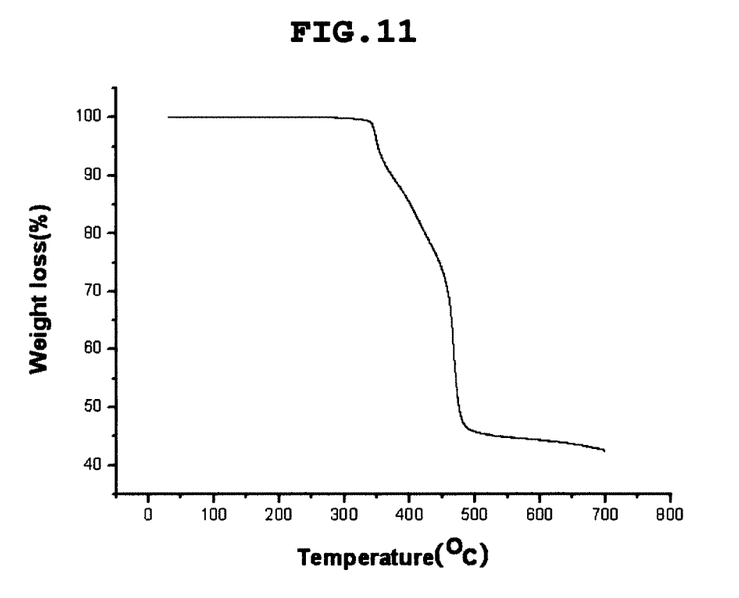
FIG. 11 is a graph showing the analysis results of a cross-linked body of a mixture of C-5 and styrene using a thermogravimetric analyzer (TGA) according to the present invention.
Figure 12:
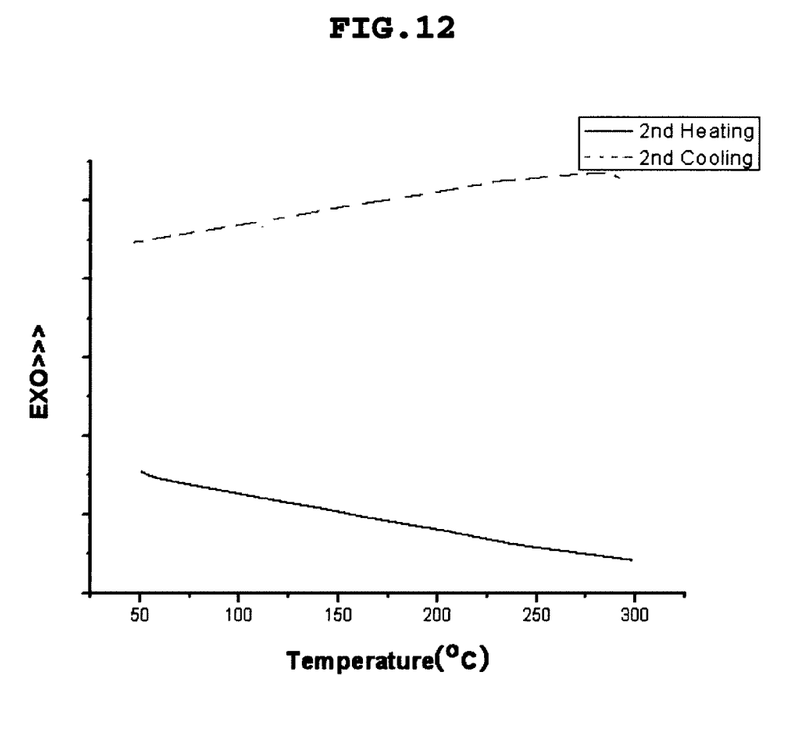
FIG. 12 is a graph showing the analysis results of a cross-linked body of a mixture of C-5 and styrene using a differential scanning calorimeter (DSC) according to the present invention.
Figure 13:
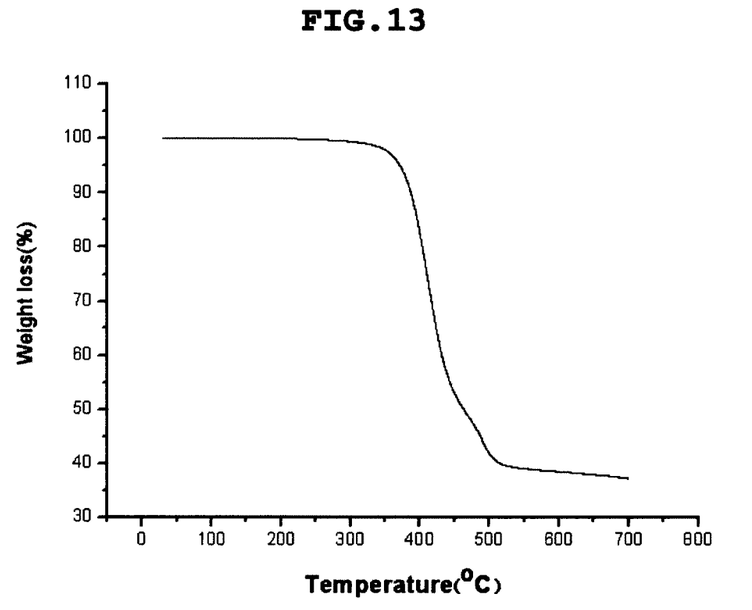
FIG. 13 is a graph showing the analysis results of a cross-linked body of a mixture of C-27 and styrene using a thermogravimetric analyzer (TGA) according to the present invention.
Figure 14:
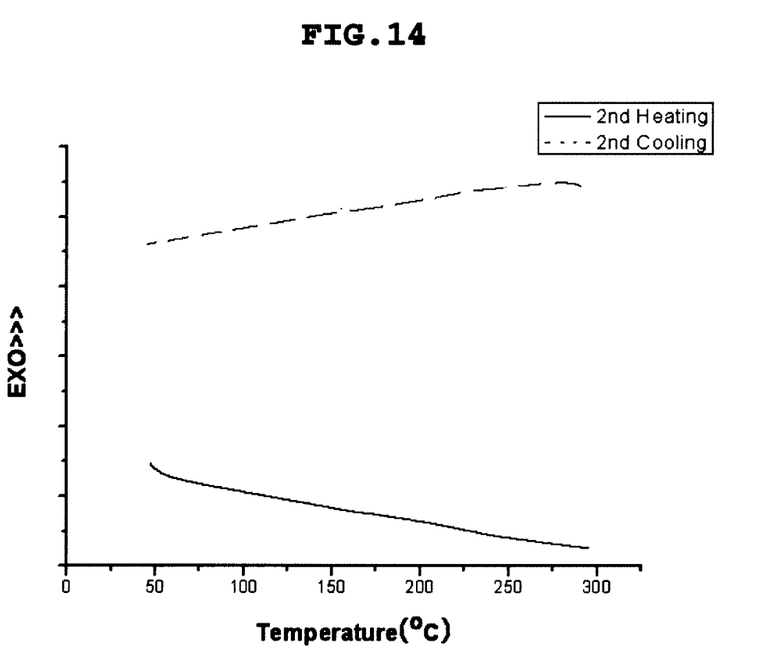
FIG. 14 is a graph showing the analysis results of a cross-linked body of a mixture of C-27 and styrene using a differential scanning calorimeter (DSC) according to the present invention.

Analysis of Thermal Properties of an Insulator Manufactured According to the Present Invention The thermal properties of the curable cyclic phosphazene compounds were analyzed using a thermogravimetric analyzer (TGA) and a differential scanning calorimeter (DSC). The analysis results thereof are shown in FIG. 1 (C-1), FIG. 3 (C-5), FIG. 4 (C-5), FIG. 5 (C-6), FIG. 6 (C-6), FIG. 7 (C-11), FIG. 8 (C-11), FIG. 9 (C-27), FIG. 10 (C-27), FIG. 11 (mixture of C-5 and styrene monomer), FIG. 12 (mixture of C-5 and styrene), FIG. 13 (mixture of C-27 and styrene) and FIG. 14 (mixture of C-27 and styrene monomer). Here, the molar ratio of C-5 or C-27: styrene monomer was 1:3.

Test Example 2

Analysis of Electrical Properties of an Insulator Manufactured According to the Present Invention Cross-linked thick films were formed by putting the curable cyclic phosphazene compounds into a die made of Teflon and then thermopolymerizing or photopolymerizing the compounds using the method described in Preparation Example 2.

The thickness of the thick film measured by a micrometer was about 700~900 μm.

The electrical properties of the cross-linked thick films were measured using a metal-insulator-metal (MIM) method, and the results thereof are given in Table 1.

TABLE 1

| Samples | Dielectric constant | Dielectric loss index |
|---|---|---|
| Cross-linked polymer of C-1 | 2.19 | 0.0050 |
| Cross-linked polymer of C-5 | 2.27 | 0.0100 |
| Cross-linked polymer of C-6 | 2.06 | 0.0047 |
| Cross-linked polymer of C-10 | 2.42 | 0.0080 |
| Cross-linked polymer of C-11 | 2.18 | 0.0027 |
| Cross-linked polymer of C-27 | 2.40 | 0.0014 |
| Cross-linked polymer of mixture of C-5 and styrene | 2.40 | 0.0013 |
| Cross-linked polymer of mixture of C-10 and styrene | 2.70 | 0.0054 |
| Cross-linked polymer of mixture of C-27 and styrene | 2.30 | 0.0010 |

As described above, a curable cyclic phosphazene compound substituted with cyclic compounds or aromatic compounds according to the present invention is advantageous in that it can be suitably used to manufacture insulating materials for next-generation substrates and insulating films for next-generation semiconductor devices because it has a low dielectric constant, a low dielectric loss index and high thermal stability.

Since a curable cyclic phosphazene compound substituted with cyclic compounds or aromatic compounds according to the present invention has a low dielectric constant, a low dielectric loss index and high thermal stability and a phosphazene compound substituted with styrene according to the present invention can be produced in large quantities at low cost, it is expected that they can be suitably used to manufacture insulating materials for next-generation substrates and insulating films for next-generation semiconductor devices.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of preparing a phosphazene polymer, wherein the phosphazene polymer is prepared by heating the curable cyclic phophazene compound represented by Formula (I) below, by dissolving the curable cyclic phosphazene compound in an organic solvent, mixing AIBN(azobisisobutyronitrile) therewith and then heating the mixture, by dissolving the curable cyclic phosphazene compound in an organic solvent, mixing cupric acetate (Cu(II) acetate) therewith as a catalyst and then heating the mixture, or by mixing the curable cyclic phosphazene compound with a photoinitiator (2,2-dimethoxy- 2-phenyl acetophenone) and then photopolymerizing the mixture using a high-pressure mercury lamp:

(I)

wherein n is 3, $R^1$ and $R^2$ are identical to or different from each other, and the sum of the numbers of $R^1$ and $R^2$ is 6;

R¹ is any one substituent selected from the group (I) consisting of methoxy, ethoxy, propyloxy, trifluoroethoxy, 1-adamantanemethoxy, 1- adamantaneethoxy, 2-norbornanemethoxy, phenoxy, 4-methylphenoxy, 4- phenylphenoxy, 1-adamantanoxy, norborneoxy, decahydronaphthalene-2-oxy and naphtalene-2-oxy, and the number of the selected R¹ is 0~4; and R² is any one curable substituent selected from the group (II) consisting of 4-vinylphenoxy, 4-ethynylphenoxy, 4'-vinyl-4-biphenyloxy, 4'-ethynyl-4- biphenyloxy and 4-(phenylethynyl)phenoxy), and the number of the selected R² is 2~6.

2. A cross-linked phosphazene polymer obtained with a method, comprising:

preparing a phosphazene polymer, wherein the phosphazene polymer is prepared by heating the curable cyclic phophazene compound represented by Formula (I) below, by dissolving the curable cyclic phosphazene compound in an organic solvent, mixing AIBN(azobisisobutyronitrile) therewith and then heating the mixture, by dissolving the curable cyclic phosphazene compound in an organic solvent, mixing cupric acetate (Cu (II) acetate) therewith as a catalyst and then heating the mixture, or by mixing the curable cyclic phosphazene compound with a photoinitiator (2,2-dimethoxy- 2-phenyl acetophenone) and then photopolymerizing the mixture using a high-pressure mercury lamp:

(I)

wherein n is 3, R¹ and R² are identical to or different from each other, and the sum of the numbers of R¹ and R² is 6;

R¹ is any one substituent selected from the group (I) consisting of methoxy, ethoxy, propyloxy, trifluoroethoxy, 1-adamantanemethoxy, 1- adamantaneethoxy, 2-norbornanemethoxy, phenoxy, 4-methylphenoxy, 4- phenylphenoxy, 1-adamantanoxy, norborneoxy, decahydronaphthalene-2-oxy and naphtalene-2-oxy, and the number of the selected R¹ is 0~4; and R² is any one curable substituent selected from the group (II) consisting of 4-vinylphenoxy, 4-ethynylphenoxy, 4'-vinyl-4-biphenyloxy, 4'-ethynyl-4- biphenyloxy and 4-(phenylethynyl)phenoxy), and the number of the selected R² is 2~6.

3. The method of preparing a phosphazene polymer according to claim 1, wherein the compound, represented by Formula (I) above, is any one selected from the compounds consisting of:

(1) a compound in which R² is a 4-vinylphenoxy group and R¹ is a trifluoroethoxy group;
(2) a compound in which R² is a 4-vinylphenoxy group and R¹ is a 1- adamantanemethoxy group;
(3) a compound in which R² is a 4-vinylphenoxy group and R¹ is a 2- norbornanemethoxy group;
(4) a compound in which R² is a 4-vinylphenoxy group and R¹ is a phenoxy group;
(5) a compound in which R² is a 4-vinylphenoxy group and R¹ is a 4-phenylphenoxy group;
(6) a compound in which R² is a 4-ethynylphenoxy group and R¹ is a trifluoroethoxy group;
(7) a compound in which R² is a 4-ethynylphenoxy group and R¹ is a 1-adamantanemethoxy group;
(8) a compound in which R² is a 4-ethynylphenoxy group and R¹ is a 2-norbornanemethoxy group;
(9) a compound in which R² is a 4-ethynylphenoxy group and R¹ is a phenoxy group;
(10) a compound in which R² is a 4-ethynylphenoxy group and R¹ is a 4-phenylphenoxy group;
(11) a compound in which R² is a 4'-vinyl-4-biphenyloxy group and R¹ is a trifluoroethoxy group;
(12) a compound in which R² is a 4'-vinyl-4-biphenyloxy group and R¹ is a 1-adamantanemethoxy group;
(13) a compound in which R² is a 4'-vinyl-4-biphenyloxy group and R¹ is a 2-norbornanemethoxy group;
(14) a compound in which R² is a 4'-vinyl-4-biphenyloxy group and R¹ is a phenoxy group;
(15) a compound in which R² is a 4'-vinyl-4-biphenyloxy group and R¹ is a 4-phenylphenoxy group;
(16) a compound in which R² is a 4'-ethynyl-4-biphenyloxy group and R¹ is a trifluoroethoxy group;
(17) a compound in which R² is a 4'-ethynyl-4-biphenyloxy group and R¹ is a 1-adamantanemethoxy group;
(18) a compound in which R² is a 4'-ethynyl-4-biphenyloxy group and R¹ is a 2-norbornanemethoxy group;
(19) a compound in which R² is a 4'-ethynyl-4-biphenyloxy group and R¹ is a phenoxy group;
(20) a compound in which R² is a 4'-ethynyl-4-biphenyloxy group and R¹ is a 4-phenylphenoxy group;
(21) a compound in which R² is a 4-(phenylethynyl)phenoxy group and R¹ is a trifluoroethoxy group;
(22) a compound in which R² is a 4-(phenylethynyl)phenoxy group and R¹ is a 1-adamantanemethoxy group;
(23) a compound in which R² is a 4-(phenylethynyl)phenoxy group and R¹ is a 2-norbornanemethoxy group;
(24) a compound in which R² is a 4-(phenylethynyl)phenoxy group and R¹ is a phenoxy group; and
(25) a compound in which R² is a 4-(phenylethynyl)phenoxy group and R¹ is a 4-phenylphenoxy group.

* * * * *